United States Patent
Park et al.

(10) Patent No.: US 9,844,610 B2
(45) Date of Patent: Dec. 19, 2017

(54) METHOD FOR PREPARING IN SITU-FORMED HYDROGEL USING ENZYME-IMMOBILIZED SUPPORT, AND BIOMEDICAL USE THEREOF

(71) Applicant: AJOU UNIVERSITY INDUSTRY-ACADEMIC COOPERATION FOUNDATION, Suwon-si, Gyeonggi-do (KR)

(72) Inventors: Ki Dong Park, Seoul (KR); Jin Woo Bae, Suwon-si (KR); Kyung Min Park, Anyang-si (KR); Eugene Lih, Seoul (KR); Bae Young Kim, Gwangju (KR); Yunki Lee, Seongnam-si (KR)

(73) Assignee: AJOU UNIVERSITY INDUSTRY-ACADEMIC COOPERATION FOUNDATION, Gyeonggi-do (KR)

( * ) Notice: Subject to any disclaimer, the term of this patent is extended or adjusted under 35 U.S.C. 154(b) by 138 days.

(21) Appl. No.: 14/429,576

(22) PCT Filed: Sep. 11, 2013

(86) PCT No.: PCT/KR2013/008202
§ 371 (c)(1),
(2) Date: Mar. 19, 2015

(87) PCT Pub. No.: WO2014/046415
PCT Pub. Date: Mar. 27, 2014

(65) Prior Publication Data
US 2015/0250890 A1     Sep. 10, 2015

(30) Foreign Application Priority Data

Sep. 19, 2012 (KR) .......................... 10-2012-0103893
Sep. 9, 2013 (KR) .......................... 10-2013-0107937

(51) Int. Cl.
*C12N 9/00* (2006.01)
*A61L 27/52* (2006.01)

(52) U.S. Cl.
CPC ........... *A61L 27/52* (2013.01); *A61L 2400/06* (2013.01)

(58) Field of Classification Search
CPC ........ A61K 47/30; A61K 47/34; A61K 47/36; A61K 47/38; A61K 47/42; A61K 9/06; A61K 9/16; A61L 2400/06; A61L 27/52; C12M 21/18; C12M 23/06; C12M 33/04
See application file for complete search history.

(56) References Cited

FOREIGN PATENT DOCUMENTS

| KR | 1020100076173 A | 7/2010 |
|---|---|---|
| KR | 1020110025530 A | 3/2011 |

OTHER PUBLICATIONS

Jin et al. Synthetic Metals (2001) 122: 237-242.*
Robinson et al. Biotechnol. Bioengineer. (1973) XV: 603-303.*
Buthe et al. in "Enzyme Stabilization and Immoblization, Methods and Protocols)" Minteer, editor; 2011 (Humana Press: New York) pp. 37-48.*
Rong Jin, et al; "Enzyme-mediated fast in situ formation of hydrogels from dextran-tyramin conjugates", Biomaterials, vol. 28, pp. 2791-2800; Available online Feb. 25, 2007.
Motoichi Kurisawa, et al; "Injectable biodegradable hydrogels compused of hyaluronic acid-tyramine conjugates for drug delivery and tissue engineering", Chem. Commun. 2005; pp. 4312-4314; First published as an Advance Article on the web Jul. 28, 2005.
Kyung Min Park, et al; "In Situ Forming Hydrogels Based on Tyramine Conjugated 4-Am-PPO-PEO via Enzymatic Oxidative Reaction", Biomacromolecules, vol. 11, pp. 706-712; Published on Web Feb. 1, 2010.
Kyung Min Park, et al; "In situ cross-linkable gelatin-poly(ethylene glycol)-tyramine hydrogel via enzyme-mediated reaction for tissue regenerative medicine", Journal of Materials Chemstry, vol. 21, pp. 13180-13187; First published online Jul. 29, 2011.
Kyung Min Park, et al; "In situ hydrogelation and RGD conjugation of tyramine-conjugated 4-arm PPO-PEO block copolymer for injectable bio-mimetic scaffolds", Soft Matter; vol. 7, pp. 986-992; First published online Nov. 29, 2010.
Kyung Min Park, et al; "Synthesis and Characterizations of In Situ Cross-Linkable Gelatin and 4-Arm-PPO-PEO Hybrid Hydrogels via Enzamatic Reaction for Tissue Regenerative Medicine", Biomacromolecules, vol. 13, pp. 604-611; Published Jan. 21, 2012.
Shinji Sakai, et al; "Synthesis and characterization of both ionically and enzymatically cross-linkable alginate", Acta Biomaterials, vol. 3, pp. 495-501, Jul. 2007 Epub Feb. 1, 2007.
Shinji Sakai, et al; "An injectable, in situ enzymatically gellable, gelatin derivative for drug delivery and tissue engineering", Biomaterials, vol. 30, pp. 3371-3377; Available online Apr. 5, 2009.
Li-Shan Wang, et al; "Injectable biodegradable hydrogels with tunable mechanical properties for the stimulation of neurogenesic differentiation of human mesenchymal stem cells in 3D culture", Biomaterials, vol. 31, pp. 1148-1157, Available online Nov. 4, 2009.
International Search Report dated Jan. 24, 2014; PCT/KR2013/008202.

(Continued)

*Primary Examiner* — Susan Hanley
(74) *Attorney, Agent, or Firm* — Ladas & Parry LLP; Loren K. Thompson

(57) ABSTRACT

The present invention relates to a method for preparing a hydrogel, including the steps of: preparing an enzyme-immobilized support; making contacting with a polymer having a phenol or aniline functional group at a side change and the support in the presence of hydrogen peroxide to cross-link the same; and obtaining a hydrogel by separating the enzyme-immobilized support. According to the present invention, a hydrogel is formed by cross-linking a polymer having a phenol or aniline functional group at a side chain through an enzyme-immobilized support, and thus a hydrogel containing no enzymes is obtained. Therefore, the biomedical application range of a hydrogel can be expanded since it is possible to overcome an in vivo safety problem such as immune reaction caused by an enzyme.

20 Claims, 10 Drawing Sheets

(56) References Cited

OTHER PUBLICATIONS

Eunji Jang, et al; "Fabrication of poly(ethylene glycol)-based hydrogels entrapping enzyme-immobilized silica nanoparticles", Polymers Advanced Technologies, vol. 21, pp. 476-482; Published online in Wiley Interscience: May 26, 2009.

Young-Jin Kim, et al; "Enzymatic Synthesis of Phenolic Polymers and Their Applications", Polymer Science and Technology, Oct. 2009, vol. 20, No. 5, pp. 465-471.

Written Opinion of the Internatinal Searching Authority dated Jan. 27, 2014; PCT/KR2013/008202.

* cited by examiner

METHOD FOR PREPARING IN SITU-FORMED HYDROGEL USING ENZYME-IMMOBILIZED SUPPORT, AND BIOMEDICAL USE THEREOF

TECHNICAL FIELD

The inventive concept relates to a method of preparing an in situ-forming hydrogel gel using an enzyme-immobilized support to improve biological safety, a biomedical use of the in situ-forming hydrogel gel, and a syringe for injecting the hydrogel having the enzyme-immobilized support.

BACKGROUND ART

A hydrogel has been widely studied as a material for pharmaceutical and biomedical applications, e.g., implants, drugs, and cell delivery carriers, based on its biocompatibility, high water contents and excellent permeability of metabolites and nutrients. Such a hydrogel can be prepared using natural and synthetic polymers and formed through a variety of chemical and physical cross-linkages. Over the past decade, the research has been focused on the improvement of an in situ-forming hydrogel prepared by injecting a polymer solution into the body to form a hydrogel in vivo.

Such an in situ-forming hydrogel can be used as an injectable hydrogel system in a living body. The injectable hydrogel system has received a lot of attention due to the ease of application forms to give comfort to a patient, based on minimal invasive techniques.

The injectable hydrogel system refers to an injectable fluid capable of forming a hydrogel in the body before being solidified in a desired tissue, organ, or body cavity, based on minimal invasive techniques.

For example, the injectable hydrogel system can be integrated through a simple mixing of many therapeutic drugs, rather than through surgical procedures for implantation. The injectable hydrogel system enables to fill a defect site or depression in the body cavity. The injectable hydrogel system generally exhibits weak mechanical properties, but has many advantages including high efficiency in cell separation, functions of a carrier for delivering a physiological active substance or a drug, such as a peptide, a protein, and DNA, and excellent transport of nutrients to cells and products.

However, the conventional injectable hydrogels developed by heat-treatment or UV irradiation have several problems in a time-consuming manufacture of a polymer solution, high solution viscosity, and slow phase transition. In order to solve such problems of the conventional in situ-forming hydrogel, an in situ-forming hydrogel using an enzyme reaction has been recently developed.

A recently developed in situ-forming hydrogel is used to develop an in situ-forming hydrogel system through an enzyme oxidation reaction occurring in the presence of horseradish peroxidase (HRP) and hydrogen peroxide ($H_2O_2$), and the in situ-forming hydrogel system overcomes disadvantages, e.g., weak mechanical strength and body stability, of the conventional hydrogel that has been prepared through a physical or chemical cross-linking reaction.

Types of an enzyme-sensitive in situ-forming hydrogels that is currently under development are as follows: Tetronic-tyramine (Tet-TA) (Park et al., Biomacromolecules 2010/2012, Soft Matter 2011), gelatin-polyethylene glycol-tyramine (GPT) (Park et al., Journal of Materials Chemistry 2011), dextran-tyramine (dec-TA) (Jin et al., Biomaterials 2007), hyaluronic acid-tyramine (HATA) (Kurisawa et al., Chem. Commun. 2005), gelatin-hydroxypropionic acid (GHPA) (Wang et al., Biomaterials 2009), gelatin-tyramine (GTA) (Sakai et al., Biomaterials 2009), alginate-tyramine (ATA) (Sakai et al., Acta Biomaterialia 2007), etc.

The enzyme-sensitive in situ-forming hydrogel includes a phenol derivative in a polymer chain, and according to a HRP-mediated coupling reaction, the phenol derivative forms a hydrogel through a carbon-carbon bond at the ortho position or a bond between a carbon at the ortho position and an oxygen of phenoxy oxygen. In addition, the enzyme-sensitive in situ-forming hydrogel has physical and chemical properties, e.g., gel formation time, mechanical strength, and biodegradability, that can be easily adjusted by adjusting the concentration of HRP and $H_2O_2$, and has advantages that a variety of physiologically active substances, drugs, and cells can be easily deposited in the hydrogel. However, the enzyme-sensitive in situ-forming hydrogel includes enzymes, e.g., HRP derived from animals and plants, formed therein, and thus, in the case of injection into the body, problems related to in vivo safety, e.g., immune responses, may occur.

DETAILED DESCRIPTION OF THE INVENTIVE CONCEPT

Technical Problem

The inventive concept provides a method of preparing a hydrogel without including an enzyme.

The inventive concept provides a hydrogel prepared by the method above and a biomedical use of the hydrogel.

The inventive concept provides a syringe for preparing a hydrogel when preparing the hydrogel.

Technical Solution

According to an aspect of the inventive concept, there are provided a method of preparing a hydrogel, the method including: preparing an enzyme-immobilized support; cross-linking the enzyme-immobilized support to a polymer including a phenol or aniline functional group at a side chain, through a contact in the presence of hydrogen peroxide; and obtaining a hydrogel by separating the enzyme-immobilized support, and a hydrogel without including an enzyme as prepared according to the method.

According to another aspect of the inventive concept, there is provided an implant material including the hydrogel for tissue regeneration and filling.

According to another aspect of the inventive concept, there is provided a carrier including the hydrogel for delivering a physiologically active substance or a drug.

According to another aspect of the inventive concept, there is provided a syringe for preparing a hydrogel, wherein, among syringes characterized by that a medicinal fluid is discharged through a syringe needle by expulsive power generated by slide operation of a built-in piston in an internal space of a syringe cylinder, an enzyme-immobilized support is provided on an inner side of an injection needle in a cylinder and a polymer including a phenol or an aniline functional group on a side chain is filled in a cylinder.

Advantageous Effects

According to the inventive concept, a polymer including a phenol or aniline functional group on a side chain is cross-liked by an enzyme immobilized on a support, thereby forming a hydrogel. In this regard, a hydrogel that does not include an enzyme is obtained, and accordingly, problems regarding in vivo safety, e.g., immune reactions caused by enzymes, can be solved. In addition, the hydrogel may extend its biomedical application ranges, and the enzyme-immobilized support used herein is reusable.

BEST MODE

Figure 1:
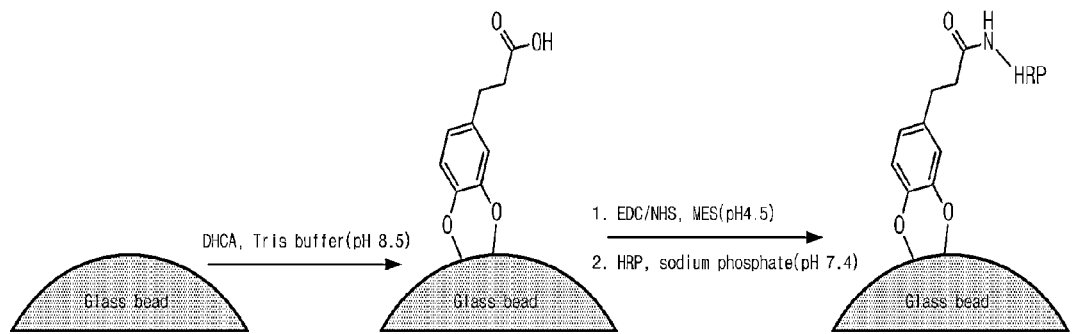
FIG. 1 is a schematic diagram illustrating a method of immobilizing a HRP enzyme on a surface of a glass particle using a dopa derivative, e.g., dopa(3,4-dihydroxyphenylalanine), and DHCA.

The inventive concept provides a method of preparing a hydrogel, the method including: preparing an enzyme-immobilized support; cross-linking the enzyme-immobilized support to a polymer including a phenol or aniline functional group at a side chain, through a contact in the presence of hydrogen peroxide; and obtaining a hydrogel by separating the enzyme-immobilized support.

An enzyme has been used as a chemical reaction catalyst in a variety of fields, based on its specific reactivity, high selectivity, and excellent reaction efficiency. However, an enzyme has been blamed for difficulties in mass production and purification, expensive price, and a decrease in the enzyme activity depending on reaction condition and storage. To improve this, studies on techniques using an enzyme in a chemical reaction according to the application purposes through chemical immobilization of the enzyme on different forms and types of a support, e.g., nano/micro microsphere, have been carried out. An enzyme-immobilized substrate prepared by the surface immobilization of the enzyme has been reported to have advantages, such as easy separation after a chemical reaction, reusability, and high storage stability as the enzyme activity is maintained. In this regard, when the inventors of the inventive concept studied a method of preparing a hydrogel using techniques of such surface immobilization of the enzyme, it was confirmed that the in situ-forming hydrogel that does not include an enzyme was obtained if an enzyme-immobilized support contacts a polymer including a phenol or an aniline functional group on a side chain in the presence of hydrogen peroxide, and is separated therefrom, thereby completing the present inventive concept.

In an exemplary embodiment, the enzyme immobilized on the surface may be one or two selected from the group consisting of horseradish peroxidase, glutathione peroxidase, haloperoxidase, myeloperoxidase, catalase, hemoprotein, peroxide, peroxiredoxin, animal heme-dependent peroxidases, thyroid peroxidase, vanadium bromoperoxidase, lactoperoxidase, tyrosinase, and catechol oxidase, but is not limited thereto.

In another exemplary embodiment, the support may be in the form of a microparticle, a porous sponge, or a porous sheet. The support in the form of the microparticle may be non-porous or porous, and may consist of a glass particle, a metal particle, a polymer particle, or a mixed particle thereof, but the embodiment is not limited thereto.

The mixed particle may be a metal-containing polymer particle, and the metal-containing polymer particle may further include iron.

In addition, the metal-containing polymer particle including iron may be prepared by copolymerization between an epoxy group-containing monomer and an iron compound.

In an exemplary embodiment, the enzyme may be immobilized to a solid phase using techniques known in the field of chromatography and immunoassay. More particularly, the preparing of the enzyme-immobilized support may include: performing surface modification on a surface of the support by introducing a functional group; and binding the enzyme to the functional group, wherein the functional group may be a carboxyl group, an amine group, a hydroxyl group, an aldehyde group, an epoxy group, a thiol group, a maleimide group, a carbonate ester group, a cyano group, an acrylic group, an acetylene group, or a diazolyl group.

The surface modification may introduce a functional group using at least one catechol derivative selected from the group consisting of 3,4-dihydroxy hydrocinnamic acid, dopamine, chloroacetylcatechol, aminomethylcatechol, deoxyepinephrine, dihydroxybenzohydrazine, caffeic acid phenethylester, and hirsutenone. However, if a compound that is structurally similar with catechol derivatives listed above, the compound and the catechol derivatives have the same chemical bonds, and thus materials used for the surface modification is not limited the list above.

In addition, the surface modification may introduce a functional group using at least one silane derivative selected from the group consisting of 3-aminopropyl triethoxysilane, trimethoxy(7-octane-1-yl)silane, vinyltrimethoxysilane, 3-trimethoxysilyl-1-propanethiol, 3-aminopropyl trimethoxysilane, aminoethyl trimethoxysilyl propylamine, triethoxyvinylsilane, isocyanatopropyl triethoxysilane, cyanoethyl triethoxysilane, mercaptopropyl triethoxysilane, and triethoxysylylpropyl diethanolamine. However, if a compound that is structurally similar with silane derivatives listed above, the compound and the silane derivatives have the same bonds, and thus materials used for the surface modification is not limited the list above.

However, if a microsupport that is a polymer bead, e.g., polystyrene bead or $SiO_2$ bead, already including a functional group on a surface is used, the binding of the enzyme without performing separate surface modification is deemed obvious to one of ordinary skill in the art.

In an exemplary embodiment, a glass particle is used as a microparticle support, and the surface modification may be performed using 3,4-dihydroxy hydrocinnamic acid (refer to Example 1, and FIG. 1) or 3-aminopropyl triethoxysilane (refer to Example 2 and FIG. 2), wherein a carboxyl functional group and an amino functional group are introduced by 3,4-dihydroxy hydrocinnamic acid and 3-aminopropyl triethoxysilane, respectively. The introduction of a functional group through the conventional surface modification techniques, e.g., chemical vapor deposition or plasma treatment, will be obvious to one of ordinary skill in the art.

The introduced functional group may be activated by using at least one coupling agent selected from the group consisting of N-Ethyl-N'-(3-dimethylaminopropyl) carbodiimide hydrochloride (EDC), N-hydroxysuccinimide (NHS), glutaraldehyde, diisothiocyanate, isocyanate, dihydroxysuccinimide, and avidin/biotin, and the enzyme is bonded to the activated functional group, thereby being immobilized on the microparticle support.

In an exemplary embodiment, in the case of a polymer particle including an iron particle, an epoxy functional group is present on a surface of the polymer particle, and thus the enzyme can be directly added without performing an additional step, thereby preparing a polymer particle in which the enzyme is chemically immobilized on the surface.

In another exemplary embodiment, a concentration of the immobilized enzyme may be in a range from about 0.001 mg/g to about 10 mg/g, about 0.1 mg/g to about 10 mg/g, or about 0.5 mg/g to about 7 mg/g, but is not limited thereto.

Here, to increase the activity of the bonded enzyme, polyethylene glycol (PEG), polyethylene oxide (PEO), polyethylene amine (PEI), polyvinyl alcohol (PVA), or polyacrylic acid (PAA), each of which has multiple functional groups, may be used as a spacer.

In another exemplary embodiment, the polymer used herein may be at least one polymer or at least two polymers selected from the group consisting of Tetronic, multifunctional polyethylene glycol, gelatin, chitosan, hyaluronic acid, heparin, cellulose, dextran, dextran sulfate, chondroitin sulfate, keratin sulfate, dermatan sulfate, alginate, collagen, albumin, fibronectin, laminin, elastin, vitronectin, and fibrinogen. The polymer used herein may include a phenol or an aniline functional group on a side chain. To introduce the phenol functional group, one or two materials selected from the group consisting of tyramine, hydroxyphenylacetic acid, hydroxypropionic acid, and a derivative thereof may be used. To introduce the aniline functional group, one or two materials selected from the group consisting of hydroxyethylaniline, aminoethylaniline, aminobenzyl alcohol, and a derivative thereof may be used. However, the embodiment is not limited thereto.

In another exemplary embodiment, the contact and separation between the polymer including the phenol or the aniline functional group on the side chain and the enzyme-immobilized support may be performed by applying pressure to pass the polymer from one side to another side of the enzyme-immobilized support, and more particularly, such a method described may be performed using a syringe kit or spray kit that is configured to spray a material at the end of a syringe.

In more detail, the polymer placed inside the syringe kit or the spray kit may pass through the enzyme-immobilized support, and then, cross-linked in situ when extruded.

In an exemplary embodiment, hydrogen peroxide may be present with a polymer having a phenol or an aniline functional group on a side chain, or may be present separately from the polymer by using a double injection syringe kit or the spray kit.

In another exemplary embodiment, the syringe kit or the spray kit may use a teflon mold to prepare a hydrogel in the form of a sheet or a disc.

To carry out such a method above, a syringe for preparing a hydrogel is provided, wherein, among syringes characterized by that a medicinal fluid is discharged through a syringe needle by expulsive power generated by slide operation of a built-in piston in an internal space of a syringe cylinder, an enzyme-immobilized support may be provided on an inner side of an injection needle in a cylinder and a polymer including a phenol or an aniline functional group on a side chain may be filled in a cylinder.

The hydrogel prepared by the method above, does not include an enzyme as confirmed in Example 6 below. In this regard, the biomedical application range of a hydrogel can be expanded since it is possible to overcome an in vivo safety problem such as immune reaction caused by an enzyme. Thus, the present inventive concept provides a hydrogel without including an enzyme, an implant material including the hydrogel for tissue regeneration and filling, and a carrier including the hydrogel for delivering a physiologically active substance or a drug.

The implant material may be used in at least one application selected from the group consisting of cartilage regeneration, bone regeneration, periodontal bond regeneration, skin regeneration, cardiac tissue regeneration, artificial intraocular lens, spinal cord regeneration, cranial regeneration, vocal regeneration and augmentation, adhesion barrier, urinary incontinence treatment, wrinkles removal, wound dressing, tissue augmentation, and intervertebral disc treatment).

In addition, when the hydrogel is used as a carrier for delivering a physiologically active substance or a drug, the physiologically active substance of the drug may be one or two selected from the group consisting of peptide or protein medicinal supplies, an antibacterial agent, an anticancer agent, and an anti-inflammatory agent The peptide or protein medicinal supplies may be selected from the group consisting of fibroblast growth factor (FGF), vascular endothelial growth factor (VEGF), transforming growth factor (TGF), bone morphogenetic protein (BMP), human growth hormone (hGH), porcine growth hormone (pGH), white blood cell growth factor (G-CSF), red blood cell growth factor (EPO), macrophage growth factor (M-CSF), tumor necrosis factor (TNF), epidermal growth factor (EGF), platelet derived growth factor (PDGF), interferon-α,β,γ, interleukin-2 (IL-2), calcitonin, nerve growth factor (NGF), growth hormone releasing factor, angiotensin, a luteinizing hormone-releasing hormone (LHRH), LHRH agonist, insulin, thyrotropin-releasing hormone (TRH), angiostatin, endostatin, somatostatin, glucagon, endorphins, bacitracin, mergain, colistin, monoclonal antibodies, vaccines, and combinations thereof.

The antibacterial agent may be selected from the group consisting of minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, and fusidic acid.

The anticancer agent may be selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D, and combinations thereof.

The anti-inflammatory agent may be selected from the group consisting of acetaminophen, aspirin, ibuprofen, diclofenac, indometacin, piroxicam, fenoprofen, flubiprofen, ketoprofen, naproxen, suprofen, loxoprofen, cinnoxicam, tenoxicam, and combinations thereof.

In an exemplary embodiment, a four arm polypropylene-oxide-polyethylene oxide polymer (trademarked by BASF under the trademark name of Tetronic™) may be used as a main chain of the polymer, a phenol derivative may be bonded thereto through tyramine (TA), thereby obtaining a Tetronic-tyramine (Tet-TA) polymer. In the presence of $H_2O_2$, the Tet-TA polymer may be in contact with the HRP-immobilized microparticle, and then, separated therefrom, thereby preparing a hydrogel from the Tet-TA polymer. In the formed hydrogel, an enzyme is not detected, and it is also confirmed that the formed hydrogel is improved in terms of gel formation time, mechanical strength of gel, and in vivo safety. In addition, the formed hydrogel is also determined to release the growth factor introduced thereto, in a sustained manner, and thus the formed hydrogel may be used as a carrier for delivering a physiologically active substance or a drug.

The hydrogel may be used in a variety of applications in the biomedical field, including in situ-forming tissue engineering scaffolds; sustained release drug delivery systems for proteins, DNA, growth factors, or cells; tissue augmentation; wound healing; and prevention of organ adhesion.

In more detail, the hydrogel may be used as an artificial extracellular matrix to create a tissue engineering scaffold.

Here, a degradation rate of the hydrogel is considered the most important regarding differentiation and growth of cells that are located in the gel, and thus a proper degradation rate needs to be controlled. For example, gelatin is degraded specifically by matrix metalloproteinase (MM), especially MMP-2 and MMP-9, that are released by the cell.

In addition, when the hydrolysis is used as a tissue engineering scaffold, its matrix stiffness also has a large influence on differentiation and growth of cells that are located in the gel. In addition, appropriately matrix stiffness is required for each cell. For example, osteocytes are known to grow well on stiff matrixes whereas soft tissue cells, e.g., fibroblasts or myoblasts, are known to grow well on soft matrixes. In a system using an enzymatic reaction, the degree to which the hydrogel is cross-linked may be easily controlled by the quantity of hydrogen peroxide, and thus the stiffness of the hydrogel may be also manipulated.

In addition, the hydrogel may be used as an artificial extracellular matrix suitable for use as a drug delivery scaffold. For example, when tyramine is introduced thereto, heparin that easily binds physically with various growth factors, heparin may retain growth factors and allow the sustained release of the growth factors (growth factor binding sites). Phenol-modified cell adhesion peptides or proteins may be used to increase cell adhesion strength inside the hydrogel matrix. Ingredients effective for the cell growth and the cell differentiation may be introduced into the used to prepare an in situ-forming artificial ECM through an enzymatic mechanism.

MODE OF THE INVENTIVE CONCEPT

Hereinafter, the present invention will be described in further detail with reference to the following examples. These examples are for illustrative purposes only and are not intended to limit the scope of the present invention.

<Example 1> Surface Immobilization of HRP Using a Dopa Derivative

Two phenolic hydroxyl groups that are present in a dopa(3,4-dihydroxyphenylalanine) derivative are known to be oxidized to the quinone form that is known to strongly bind to the surface of various materials, and accordingly, a functional group can be introduced, the functional group being used for chemical immobilization of the enzyme on the surface of a polymer including glass particles and the surface of metal particles. In addition, a coupling agent can be also used to immobilize HRP.

FIG. 1 is a schematic diagram illustrating a method of immobilizing a HRP enzyme on a surface of a glass particle using a dopa derivative, e.g., dopa(3,4-dihydroxyphenylalanine), and 3,4-dihydroxyhydrocinnamic acid (DHCA). Detailed procedure is as follows.

First, DHCA was put in a Tris buffer solution (10 mM, pH 8.5) to allow a reaction at room temperature for 12 hours, so as to obtain the glass particle (a diameter of about 212 μm to about 300 μm) to which DHCA was bound on the surface. The glass particle to which a carboxyl group was introduced was activated in a 2-(N-morpholino)ethanesulfonic acid (MES) buffer solution (0.1 M, pH 4.5) for 2 hours using N-ethyl-N'-(3-dimethylaminopropyl)carbodiimide hydrochloride (EDC) and N-hydroxysuccinimide (NHS), and then, the excess of EDC and NHS was washed and removed with PBS and distilled water.

Next, the activated glass particle was dispersed in sodium phosphate (0.1M, pH 7.2), and then, a HRP solution was added thereto to allow a reaction at room temperature for 6 hours. The residual HRP and the HRP absorbed on the surface of the glass particle were washed and removed with the excess of PBS and distilled water, thereby obtaining a HRP-immobilized glass particle.

<Example 2> Surface Immobilization of HRP Using Silanization

Figure 2:
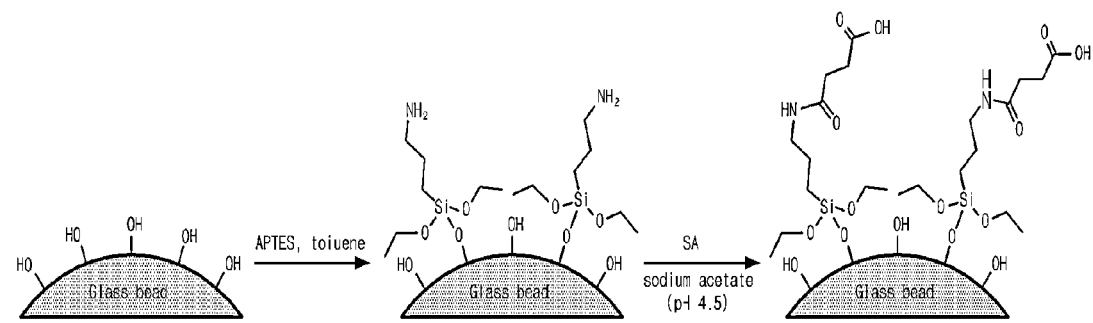
FIG. 2 is a schematic diagram illustrating a method of immobilizing a HRP enzyme on a surface of a glass particle by introducing a carboxyl group and using EDC/NHS after performing silanization.

FIG. 2 is a schematic diagram illustrating a method of immobilizing the HRP enzyme on the surface of the glass particle by introducing a carboxyl group and using the EDC/NHS after performing silanization. According to a chemical reaction to be used in the reaction illustrated in the figure, various silane coupling agent other than 3-aminopropyl triethoxysilane (APTES) can be used. In addition, to carry out the surface immobilization of the HRP after performing silanization, various chemical functional groups can be introduced, and accordingly various coupling agents, e.g., glutaraldehyde, diisothiocyanate, dihydroxysuccinimide, and avidin/biotin, can be used. Here, to increase the enzyme activity, polyethylene glycol (PEG) can be used as a spacer.

A. HRP Immobilization Using EDC/NHS

FIG. 2 illustrates a method of immobilizing the HRP on the surface of the glass particle by introducing a carboxyl group and using the EDC/NHS after performing silanization. Detailed procedure is as follows.

First, the glass particle was washed with a piranha solution (sulfuric acid:hydrogen peroxide=3:1) and dried with nitrogen. The washed glass particle was put in 2 vol % APTES solution that was prepared using toluene, to allow a reaction at room temperature for 5 hours. After the reaction was completed, the glass particle used in the reaction was washed with toluene, and then, backed at a temperature of 110° C. for 1 hour, so as to obtain a glass particle to which an amine group was introduced. Afterwards, the backed glass particle was put in 5 wt % succinic anhydride (SA) solution to allow a reaction at room temperature for 24 hours, so as to obtain a glass particle to which a carboxyl group was introduced. Then, the obtained glass particle was washed with the excess of PBS and distilled water, so as to remove the residual SA.

The glass particle was put in MES buffer solution containing EDC and NHS, to allow a reaction for 2 hours, and then, washed to obtain a glass particle to which the carboxyl group was activated. Finally, the HRP was subjected to a reaction for 6 hours, thereby obtaining a HRP-immobilized glass particle.

B. HRP Immobilization Using Glutaraldehyde

To obtain a glass particle to which an aldehyde group was introduced by performing glutaraldehyde treatment, 1 g of the glass particle to which the amine group was introduced was added to 2.5 wt % glutaraldehyde solution using APTES, and then, the mixed solution was stirred at room temperature for 12 hours. Then, the glass particle of which the surface was activated by the aldehyde group was washed with PBS and distilled water, and separated therefrom. Next, the glass particle was put in a sodium phosphate buffer (0.05 M, pH 7), and the HRP was added thereto, to allow a reaction at a temperature of 4° C. for 12 hours. After the reaction was completed, the HRP-immobilized glass particle was washed with PBS and distilled water, and then, dried.

<Example 3> HRP Immobilization Using an Iron Ion-Containing Support

Figure 3:
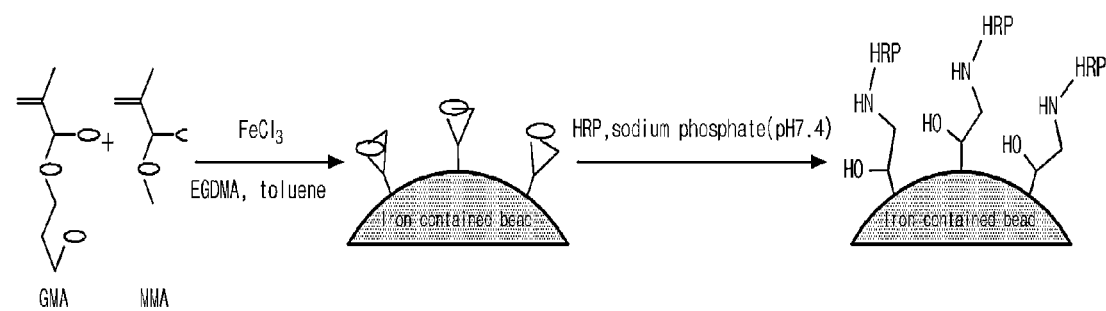
FIG. 3 is a schematic diagram illustrating a method of immobilizing a HRP enzyme on a surface of a support after preparing a microparticle polymer that contains an iron particle through copolymerization of an iron compound and an epoxy group-containing monomer.

FIG. 3 is a schematic diagram illustrating a method of immobilizing the HRP enzyme on a surface of a support prepared by copolymerizing iron chloride and a monomer including an epoxy functional group. An iron ion included in the prepared copolymer may directly induce a production of hydroxyl radicals or a synergistic effect to help the function of the HRP enzyme. The monomer used herein may use various functional groups in addition to the epoxy functional group according to a desired chemical reaction. Detailed procedure is as follows.

Glycidyl methacrylate (GMA), which is a vinyl-based monomer including an iron chloride molecule and an epoxy group, methyl methacrylate (MMA), and ethylene glycol dimethacrylate (EGDMA), which is used as a cross-linking agent, were used and stirred at a temperature of about 80° C. for 3 hours. The resultant products were washed with ethanol and distilled water, and then, dried, so as to obtain an iron ion-containing polymer particle.

The immobilization can be easily carried out through a binding between the epoxy functional group of the prepared polymer particle and the amine group of the HRP enzyme. 1 g of the polymer particle was stirred for about 30 minutes to be dispersed in PBS, and then, HRP solution was added thereto, to allow a reaction at room temperature for 2 hours. The residual HRP and the HRP absorbed on the surface of the support were washed and removed with the excess of PBS and distilled water, thereby obtaining a HRP-immobilized support.

<Example 4> Quantification of Immobilized HRP

The HRP prepared according to the immobilization methods of Examples 1 and 2 above and the HRP concentrations in used was subjected to quantitative analysis using the micro BCA analysis method, and the analysis method is as follows.

0.1 g of the HRP-immobilized particle sample was put in a tube, and then, was subjected to pre-wetting in 1 mL of PBS solution for 1 hour. Then, 1 mL of BCA solution was added thereto, to allow incubation at a temperature of 60° C. for 1 hour. The UV absorbance of the supernatant (1 ml) was measured at 562 nm, and the measurements were subjected to absorbance analysis according to the concentrations of the standard solution of albumin, so that the concentrations of the HRP were confirmed.

The results are shown in Tables 1 to 3 below. Table 1 shows the results regarding the HRP immobilization according to Example 1, Table 2 shows the results regarding the HRP immobilization according to Example 2 (A), and Table 3 shows the results regarding the HRP immobilization according to Example 2 (B). In addition, Table 4 shows the results regarding the HRP immobilization according to Example 3.

TABLE 1

| Amounts of glass particles (g) | HRP concentration in use (mg/mL) | Amounts of immobilized HRP (µg) |
| --- | --- | --- |
| 1 | 0.5 | 387 |
| 1 | 2.5 | 655 |
| 1 | 5 | 805 |

TABLE 2

| Amounts of glass particles (g) | HRP concentration in use (mg/mL) | Amounts of immobilized HRP (µg) |
| --- | --- | --- |
| 1 | 0.5 | 51 |
| 1 | 2.5 | 80 |
| 1 | 5 | 114 |

TABLE 3

| Amounts of glass particles (g) | HRP concentration in use (mg/mL) | Amounts of immobilized HRP (µg) |
| --- | --- | --- |
| 1 | 0.5 | 72 |
| 1 | 2.5 | 105 |
| 1 | 5 | 146 |

TABLE 4

| Amounts of iron-containing polymer particles (g) | HRP concentration in use (mg/mL) | Amounts of immobilized HRP (μg) |
|---|---|---|
| 1 | 0.5 | 369 |
| 1 | 2.5 | 821 |
| 1 | 5 | 1103 |

<Example 5> Preparation of Synthetic Copolymer Including a Phenol Group

1. Synthesis of Tetronic-Tyramine (Tet-TA)

Figure 4:
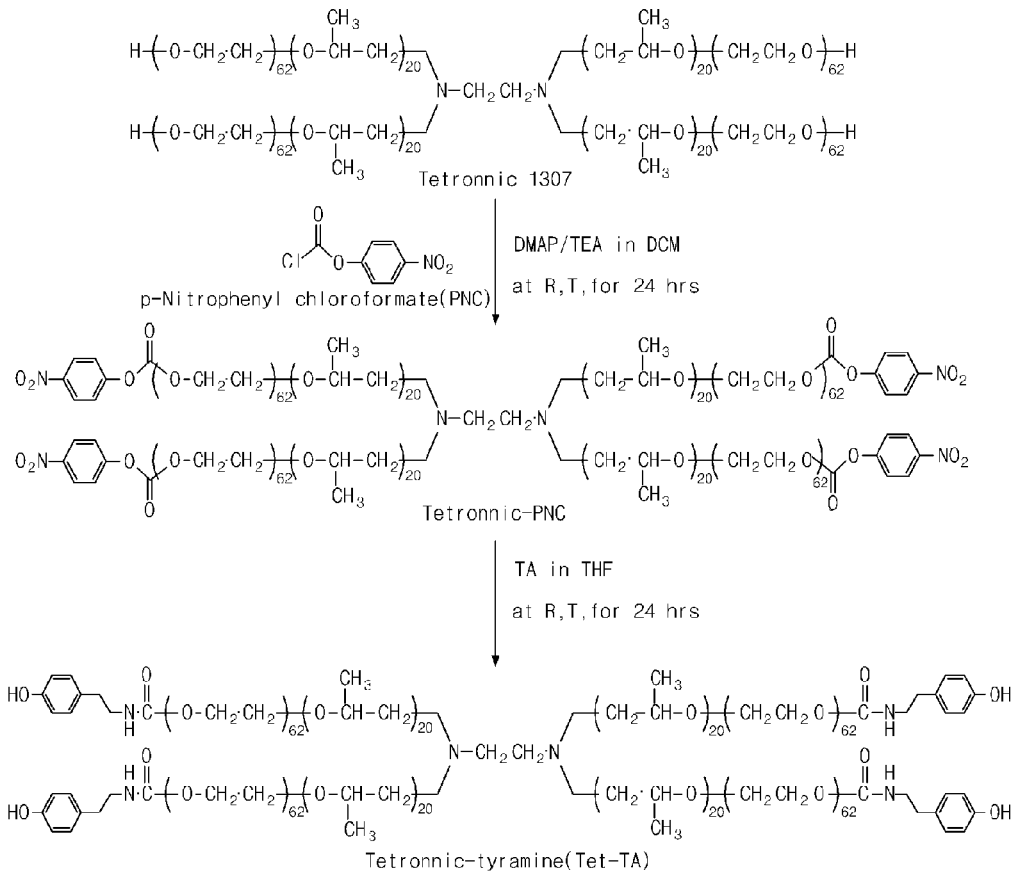
FIG. 4 is a schematic diagram illustrating synthesis of Tetronic-tyramine (Tet-TA) that is a polymer including a phenol functional group on a side chain.

FIG. 4 is a schematic diagram illustrating synthesis of Tet-TA that is a synthetic copolymer to which a phenol group is bound. Detailed procedure is as follows.

30 g (1.67 mmol) of Tetronic was dissolved in 300 ml of dioxane, 1.018 g (8.33 mmol) of 4-dimethylaminopyridine (DMPA) and 0.843 g (8.33 mmol) of trietiamine (TEA) were dissolved in 40 ml of dioxane, and 1.679 g (8.33 mmol) of p-nitrophenylchloroformate (PNC) was dissolved in 50 ml of dioxane. Then, these 3 mixed solutions were mixed in sequence.

A molar ratio of Tetronic:succinic anhydride:DMAP:TEA was 1:5:5:5. Here, the reaction was allowed at a temperature of 30° C. for 24 hours in a nitrogen atmosphere. After the reaction was completed, a filter was used to remove residual reagents from the reaction solution, and then, a rotating evaporator was used to concentrate the reaction solution. 1,600 ml of cold ether was slowly added in drops thereto to produce precipitates, and the precipitates were filtered through a filter, so as to obtain the resultant products. The obtained resultant products were placed in a vacuum oven for 24 hours to remove the residual organic solvents, thereby obtaining Tetronic-PNC in the form of white powder.

Afterwards, 20 g (1.11 mmol) of Tetronic-PNC was added to a mixture of a solution in which 0.761 g (5.55 mmol) of tyramine (TA) was dissolved in 150 ml of THF and a solution in which 200 ml of tetrahydrofuran (THF) was dissolved, to allow a reaction. Here, a molar ratio of Tetronic-PNC:TA was 1:5. The reaction was allowed at a temperature of 30° C. in a nitrogen atmosphere for 24 hours.

After the reaction was completed, the reaction solution was subjected to membrane dialysis (3,500 Da molecular weight cut off) using acetone, to remove TA that was not involved in the reaction. After the dialysis was completed, the reaction solution was filtered through a filter, and then, concentrated using a rotating evaporator. 1,600 ml of cold ether was slowly added thereto to produce precipitates, and the precipitates were filtered through a filter, and then, placed in a vacuum oven for 24 hours, thereby obtaining non-degradable Tet-TA the form of white powder.

2. Synthesis of Gelatin-Hydroxyphenylacetate (GHPA)

Figure 5:
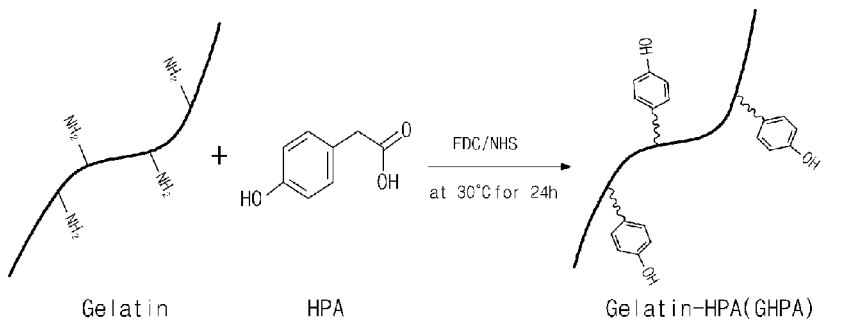
FIG. 5 is a schematic diagram illustrating synthesis of gelatin-hydroxypropionic acid (GHPA) that is a polymer including a phenol functional group on a side chain.

FIG. 5 is a schematic diagram illustrating synthesis of GHPA. Detailed procedure is as follows.

10 g of gelatin was dissolved in 200 ml of 0.1 M 2-(N-morpholino)ethanesulfonic acid (MES), so as to prepare Solution A. 0.609 g (4 mmol) of 4-hydroxyphenylacetate (HPA) was dissolved in 50 ml of 0.1 M MES, so as to prepare Solution B. 0.92 g (4.8 mmol) of 1-ethyl-3-(3-dimethylaminopropyl)-carbodiimide (EDC) and 0.276 g (2.4 mmol) of N-hydroxysuccinimide (NHS) were each dissolved in 5 ml of 0.1 M MES. Afterwards, the EDC solution and the NHS solution were sequentially added to Solution B at 5 minute intervals. After 15 minutes, Solution B including the EDC/NHS solutions was mixed with Solution A, to allow a reaction.

Here, the reaction was carried out at a temperature of 40° C. for 24 hours. After the reaction was completed, the reaction solution was filtered through a syringe filter (450 nm). Afterwards, the filtered reaction solution was subjected to membrane dialysis (500 Da molecular weight cut off) for about 3 to 4 days in distilled water. The resultant solution was freeze-dried, thereby obtaining GHPA in the form of white powder.

3. Synthesis of Chitosan-Hydroxyphenylacetic Acid (CHPA)

Figure 6:
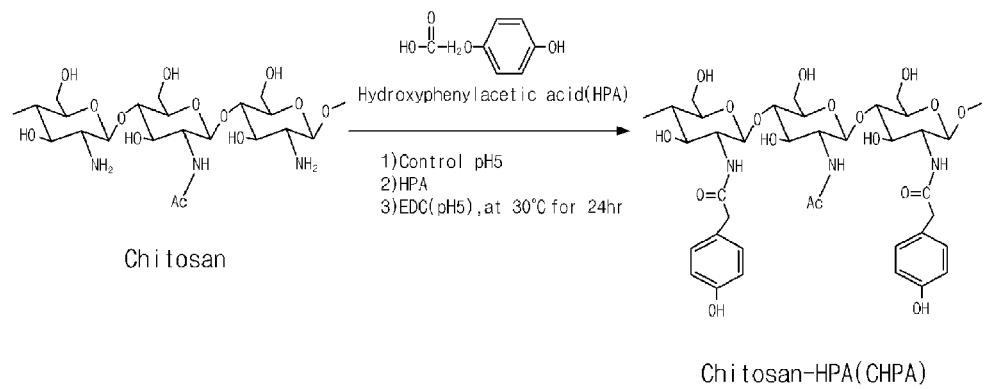
FIG. 6 is a schematic diagram illustrating synthesis of chitosan-hydroxyphenylacetic acid (CHPA) that is a polymer including a phenol functional group on a side chain.

FIG. 6 is a schematic diagram illustrating synthesis of CHPA. Detailed procedure is as follows.

0.644 g of chitosan having a low molecular weight (diacetylation of 75% to 85%) was added to 80 ml of distilled water, and then, 1N HCl was used to lower a pH of the mixed solution to pH 3 during dissolution. 0.404 g (2.6 mmol) of HPA was added thereto, and then, 0.1 M NaOH was used to lower a pH of the mixed solution to pH 5. 0.768 g (4 mmol) of EDC was added thereto, to allow a reaction at a temperature of 30° C. for 24 hours.

After the reaction was completed, the reaction solution was subjected to membrane dialysis (3,500 Da molecular weight cut off) in distilled water, so as to remove HPA that was not involved in the reaction. The resultant solution was freeze-dried, thereby obtaining CHPA in the form of semi-transparent non-woven fabric.

4. Synthesis of Gelatin-Poly(Ethyleneglycol)-Tyramine (GPEG-TA)

Figure 7:
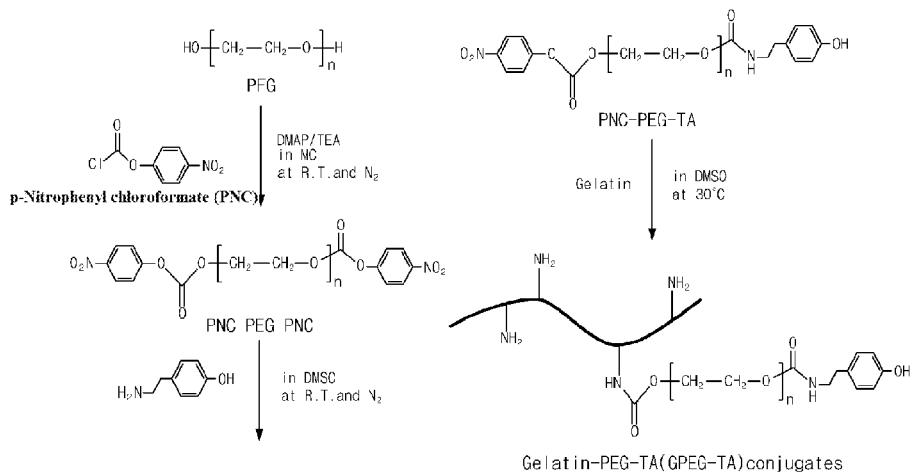
FIG. 7 is a schematic diagram illustrating synthesis of gelatin-poly(ethyleneglycol)-tyramine (GPEG-TA) that is a polymer including a phenol functional group on a side chain.

FIG. 7 is a schematic diagram illustrating synthesis of GPEG-TA. Detailed procedure is as follows.

1) Synthesis of Poly(Ethylene Glycol)-(p-Nitrophenyl Chloroformate) (PEG-PNC)

A solution in which 10 g (2.9 mmol) of PEG was dissolved in 100 ml of methylene chloride (MC) was sequentially mixed with a solution in which 0.779 g (6.38 mmol) of DMAP and 0.645 g (6.38 mmol) of TEA were dissolved in 10 ml of MC and a solution 1.286 g (6.38 mmol) of PNC was dissolved in 50 ml of MC. Here, a molar ratio of PEG:DMAP:TEA:PNC was 1:2.2:2.2:2.2, and the reaction was carried out at a temperature of 30° C. in a nitrogen atmosphere for 24 hours.

After the reaction was completed, a filter was used to remove residual reagents from the reaction solution, and then, a rotating evaporator was used to concentrate the reaction solution. 1,600 ml of cold ether was slowly added in drops thereto to produce precipitates, and the precipitates were filtered through a filter, so as to obtain the resultant products. The obtained resultant products were placed in a vacuum oven for 24 hours to remove the residual organic solvents, thereby obtaining PEG-PNC in the form of white powder.

2) Synthesis of GPEG-TA

A solution in which 5 g (1.471 mmol) of PEG-PNC was dissolved in 100 ml of DMSO was added to a solution in which 0.202 g (1.471 mmol) of TA was dissolved in 50 ml of DMSO, to allow a reaction. Here, a molar ratio of PEG-PNC:TA was 1:1, and the reaction was carried out at a temperature of 30° C. in a nitrogen atmosphere for 6 hours. After 6 hours, a gelatin solution (1 g/200 ml in DMSO) was added thereto, and a reaction was carried out at a temperature of 30° C. in a nitrogen atmosphere for 24 hours.

After the reaction was completed, the reaction solution was subjected to membrane dialysis (6,000 to 8,000 Da weight cut off) in water, to remove PEG-TA that was not involved in the reaction. After the dialysis was completed, the reaction solution was freeze-dried, thereby obtaining GPEG-TA in the form of white powder.

5. Synthesis of Chitosan-Poly(Ethyleneglycol)-Tyramine (CPTA)

Figure 8:
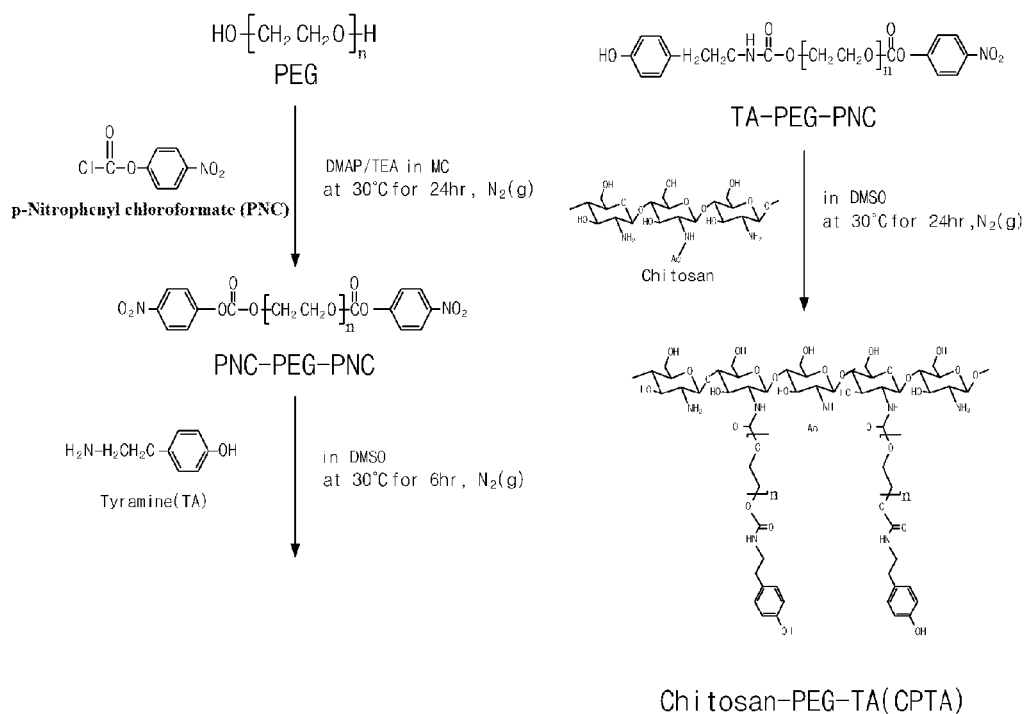
FIG. 8 is a schematic diagram illustrating synthesis of chitosan-poly(ethylene glycol)-tyramine (CPTA) that is a polymer including a phenol functional group on a side chain.

FIG. 8 is a schematic diagram illustrating synthesis of CPTA. Detailed procedure is as follows.

A solution in which 5 g (1.25 mmol) of PEG-PNC was dissolved in 100 ml of DMSO was added to a solution in which 0.174 g (1.25 mmol) of TA was dissolved in 50 ml of DMSO, to allow a reaction. Here, a molar ratio of PEG-PNC:TA was 1:1, and the reaction was carried out at a temperature of 30° C. in a nitrogen atmosphere for 6 hours. After 6 hours, the reaction solution was mixed with a solution in which 0.5 g of chitosan was dissolved in 50 ml of DMSO containing acetic acid (70 wt %) in a reaction flask, to allow a reaction at a temperature of 30° C. in a nitrogen atmosphere for 24 hours.

After the reaction was completed, the reaction solution was subjected to membrane dialysis (6,000 to 8,000 Da weight cut off) in water, to remove PEG-TA that was not involved in the reaction. After the dialysis was completed, the reaction solution was freeze-dried, thereby obtaining CPTA) in the form of white powder.

6. Synthesis of Hyaluronic Acid-Poly(Ethyleneglycol)-Tyramine (HA-PEG-TA)

Figure 9:
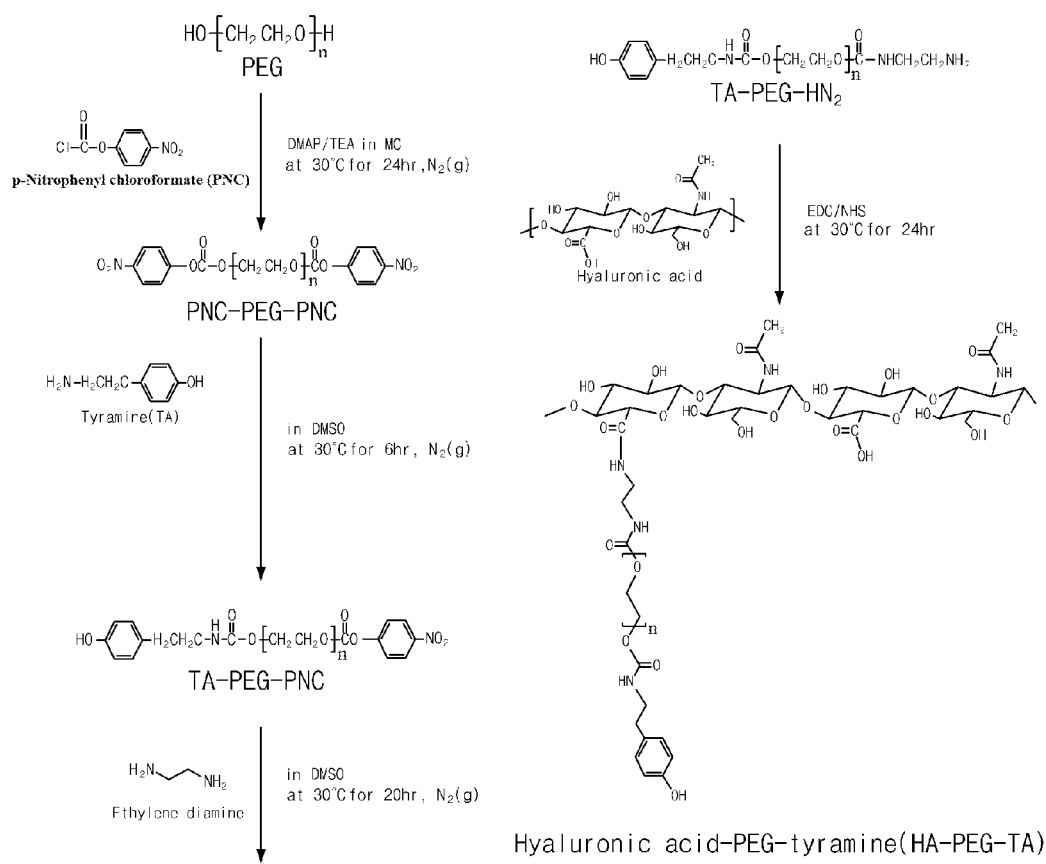
FIG. 9 is a schematic diagram illustrating synthesis of hyaluronic acid-poly(ethyleneglycol)-tyramine (HA-PEG-TA) that is a polymer including a phenol functional group on a side chain.

FIG. 9 is a schematic diagram illustrating synthesis of HA-PEG-TA. Detailed procedure is as follows.

1) Synthesis of Aminated Poly(Ethylene Glycol)-Tyramine (PTA)

A solution in which 5 g (1.25 mmol) of PEG-PNC was dissolved in 100 ml of MC was added to a solution in which 0.174 g (1.25 mmol) of TA was dissolved in 50 ml of MC, to allow a reaction. Here, a molar ratio of PEG-PNC:TA was 1:1, and the reaction was carried out at a temperature of 30° C. in a nitrogen atmosphere for 6 hours. After 6 hours, a solution in which 2.254 g (37.5 mmol) of ethylenediamine was dissolved in 50 ml of MC was added thereto, and a reaction was carried out at a temperature of 30° C. in a nitrogen atmosphere for 24 hours. Here, a molar ratio of PEG-PNC:ethylenediamine was 1:30.

After the reaction was completed, a filter was used to remove residual reagents from the reaction solution, and then, a rotating evaporator was used to concentrate the reaction solution. 1,600 ml of cold ether was slowly added in drops thereto to produce precipitates, and the precipitates were filtered through a filter, so as to obtain the resultant products. The obtained resultant products were placed in a vacuum oven for 24 hours to remove the residual organic solvents, thereby obtaining PTA in the form of white powder.

2) Synthesis of HA-PEG-TA 1.307 g (6.82 mmol) of EDC and 0.392 g (3.41 mmol) of NHS were each added at 15 minute intervals to a solution in which 1 g of HA was dissolved in 300 ml of distilled water. Afterwards, a solution in which 2.5 g (0.625 mmol) of PTA was dissolved in 100 ml of distilled water was added to the reaction flask, to allow a reaction at a temperature of 30° C. for 24 hours.

After the reaction was completed, a filter was used to remove residual reagents from the reaction solution, and then, the reaction solution was subjected to membrane dialysis (6,000 to 8,000 Da weight cut off) for about 3 to 4 days in distilled water. After the dialysis was completed, the reaction solution was freeze-dried, thereby obtaining HA-PEG-TA in the form of white powder.

7. Synthesis of Carboxymethyl Cellulose-Poly(Ethyleneglycol)-Tyramine (CMC-PEG-TA)

Figure 10:
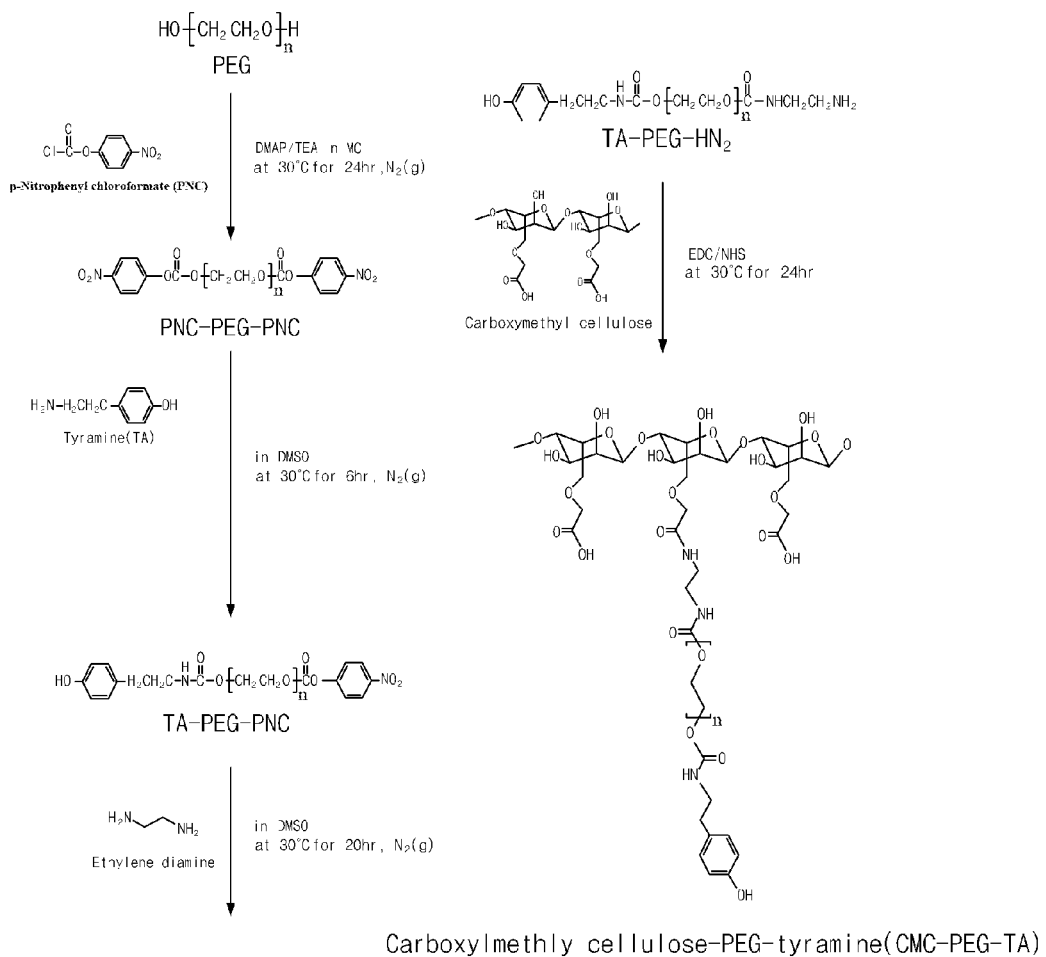
FIG. 10 is a schematic diagram illustrating synthesis of carboxymethyl cellulose-poly(ethyleneglycol)-tyramine (CMC-PEG-TA) that is a polymer including a phenol functional group on a side chain.

FIG. 10 is a schematic diagram illustrating synthesis of CMC-PEG-TA. Detailed procedure is as follows.

1.307 g (6.82 mmol) of EDC and 0.392 g (3.41 mmol) of NHS were each added at 15 minute intervals to a solution in which 1 g of CMC was dissolved in 300 ml of distilled water. Afterwards, a solution in which 2.5 g (0.625 mmol) of PTA was dissolved in 100 ml of distilled water was added to the reaction flask, to allow a reaction at a temperature of 30° C. for 24 hours.

After the reaction was completed, a filter was used to remove residual reagents from the reaction solution, and then, the reaction solution was subjected to membrane dialysis (6,000 to 8,000 Da weight cut off) for about 3 to 4 days in distilled water. After the dialysis was completed, the reaction solution was freeze-dried, thereby obtaining CMC-PEG-TA in the form of white powder.

8. Synthesis of Alginate-Poly(Ethyleneglycol)-Tyramine (ALG-PEG-TA)

Figure 11:
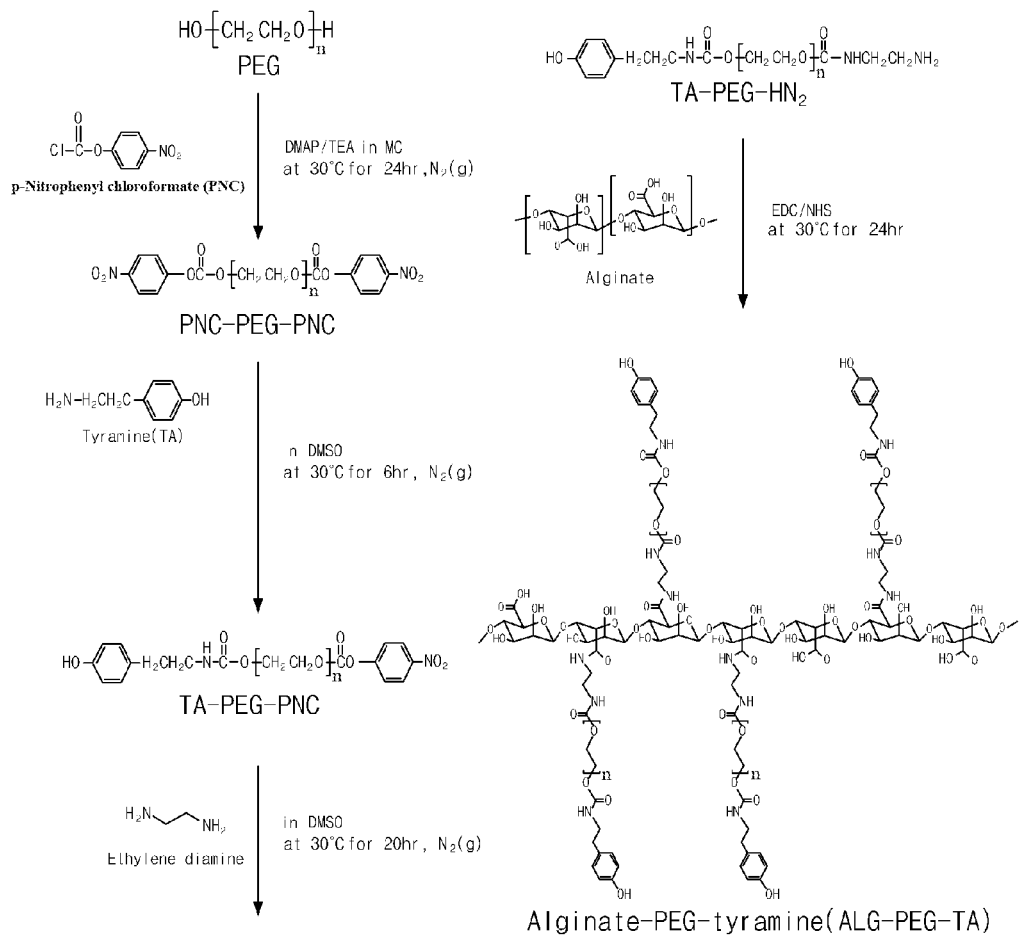
FIG. 11 is a schematic diagram illustrating synthesis of alginate-poly(ethyleneglycol)-tyramine (ALG-PEG-TA) that is a polymer including a phenol functional group on a side chain.

FIG. 11 is a schematic diagram illustrating synthesis of ALG-PEG-TA. Detailed procedure is as follows.

1.307 g (6.82 mmol) of EDC and 0.392 g (3.41 mmol) of NHS were each added at 15 minute intervals to a solution in which 1 g of ALG was dissolved in 300 ml of distilled water. Afterwards, a solution in which 2.5 g (0.625 mmol) of PTA was dissolved in 100 ml of distilled water was added to the reaction flask, to allow a reaction at a temperature of 30° C. for 24 hours.

After the reaction was completed, a filter was used to remove residual reagents from the reaction solution, and then, the reaction solution was subjected to membrane dialysis (6,000 to 8,000 Da weight cut off) for about 3 to 4 days in distilled water. After the dialysis was completed, the reaction solution was freeze-dried, thereby obtaining ALG-PEG-TA in the form of white powder.

<Example 6> Preparation of Injectable Hydrogel Using HRP-Immobilized Particles and Quantitative Results of HRP The phenol group-containing polymer compounds (10%, Examples 5-1 to 5-8) as synthesized according to Example 5 and 500 μL of the mixed solution with 0.1% hydrogen peroxide were added to syringes that were filled with the glass particle and the iron-containing particle, each of which particles had different amounts of the immobilized HRP, and then, the syringes were subjected to extrusion. To compare physical and chemical properties of each particle, the quantitative analysis was carried out by using a microparticle having the same amount of the immobilized HRP after the gel was formed.

Figure 12:
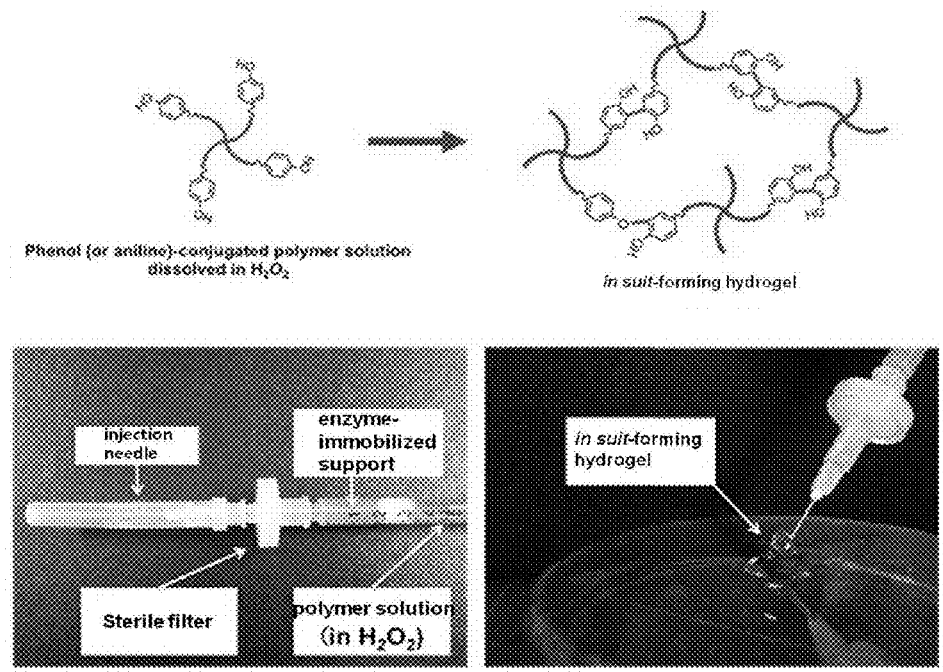
FIG. 12 is a schematic diagram illustrating a syringe and formation of a gel according to an exemplary embodiment.
Figure 13:
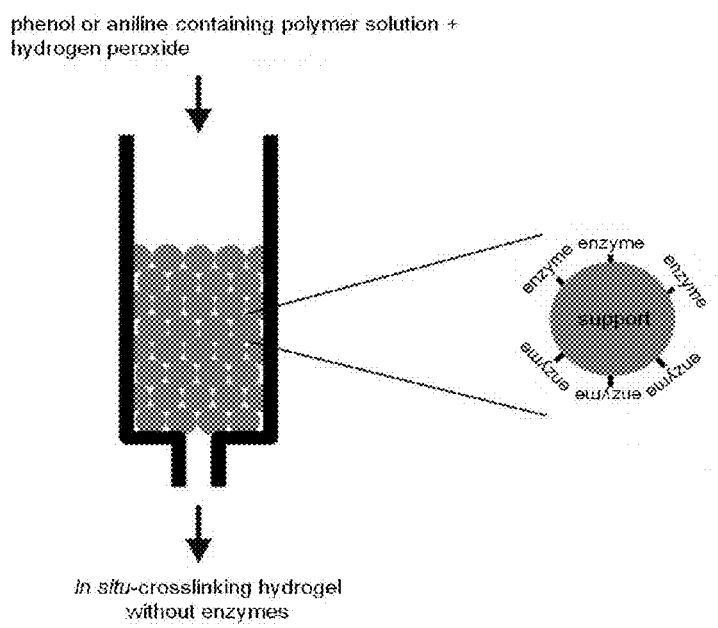
FIG. 13 is a schematic diagram illustrating a cross-sectional view of a syringe and formation of a hydrogel according to an exemplary embodiment.

FIGS. 12 and 13 are a schematic diagram illustrating a syringe used in the gel formation and a schematic diagram illustrating the gel formation, respectively. FIG. 12 is a diagram illustrating a syringe used in an exemplary embodiment, wherein an enzyme-immobilized support is provided on an inner side of an injection needle in a cylinder, and the cylinder is filled with the phenol group-containing polymer compounds (Examples 5-1 to 5-8) (10%) and 500 μL of the mixed solution with 0.1% hydrogen peroxide. Then, upon the slide operation of a built-in piston, the mixed solution was passed through the enzyme-immobilized support, and in the case of being discharged from the injection needle, a cross-linked, in situ-hydrogel was formed.

FIG. 13 is a schematic diagram illustrating a cross-sectional view of the syringe and formation of a hydrogel according to an exemplary embodiment. The HRP quantitative values of the formed hydrogel using the micro BCA analysis method are shown in Tables 5 and 6 below.

TABLE 5

| HRP quantitative values of formed hydrogel (mg/mL) | Amounts of glass particles (g) (146 ug of HRP/g of bead) | | |
|---|---|---|---|
| | 0.5 | 1.0 | 2.0 |
| Tet-TA(Example 4-1) | N.D. | N.D. | N.D. |
| GHPA(Example 4-2) | N.D. | N.D. | N.D. |
| CHPA(Example 4-3) | N.D. | N.D. | N.D. |
| GPEG-TA(Example 4-4) | N.D. | N.D. | N.D. |
| CPTA(Example 4-5) | N.D. | N.D. | N.D. |
| HA-PEG-TA (Example 4-6) | N.D. | N.D. | N.D. |
| CMC-PEG-TA (Example 4-7) | N.D. | N.D. | N.D. |
| ALG-PEG-TA (Example 4-8) | N.D. | N.D. | N.D. |

N.D.: Not detected.

TABLE 6

| HRP quantitative values of formed hydrogel (mg/mL) | Amounts of iron-containing polymer particles (g) (369 ug of HRP/g of bead) | | |
|---|---|---|---|
| | 0.2 | 0.4 | 0.8 |
| Tet-TA (Example 4-1) | N.D. | N.D. | N.D. |
| GHPA (Example 4-2) | N.D. | N.D. | N.D. |
| CHPA (Example 4-3) | N.D. | N.D. | N.D. |
| GPEG-TA (Example 4-4) | N.D. | N.D. | N.D. |
| CPTA (Example 4-5) | N.D. | N.D. | N.D. |
| HA-PEG-TA (Example 4-6) | N.D. | N.D. | N.D. |
| CMC-PEG-TA (Example4-7) | N.D. | N.D. | N.D. |
| ALG-PEG-TA (Example4-8) | N.D. | N.D. | N.D. |

N.D.: Not detected.

Referring to Tables 5 and 6 above, it was confirmed that the enzyme was immobilized on the support and were not discharged from the syringe needle, and accordingly, the hydrogel that did not include the enzyme was obtained.

<Experimental Example 1> Review on Formation Time/Mechanical Strength of Gel

The HRP-immobilized microparticle was quantified to have the same amount of the HRP in a syringe, and then, filled therein. When the phenol group-containing polymer compounds (10%, Examples 5-1 to 5-8) of Example 5 and 500 μL of the mixed solution with 0.1% hydrogen peroxide were added to a syringe, and the syringe was subjected to extrusion, the formation time of hydrogel and mechanical strength of the formed hydrogel according to the amounts of the HRP-immobilized microparticle are shown in Table 7 and 8 below.

TABLE 7

| | Amounts of glass particle (g) 146 ug of HRP/g of bead | Hydrogel formation time (sec) | Hydrogel mechanical strength (KPa) |
|---|---|---|---|
| Tet-TA | 0.5 | 70 | 8.6 |
| | 1.0 | 44 | 9.3 |
| | 2.0 | 20 | 10.5 |
| GHPA | 0.5 | 41 | 3.1 |
| | 1.0 | 29 | 7.9 |
| | 2.0 | <5 | 11.2 |
| CHPA | 0.5 | 95 | 0.7 |
| | 1.0 | 66 | 1.9 |
| | 2.0 | 38 | 3.5 |
| GPEG-TA | 0.5 | 62 | 6.1 |
| | 1.0 | 40 | 8.6 |
| | 2.0 | 16 | 9.8 |
| CPTA | 0.5 | 50 | 1.2 |
| | 1.0 | 32 | 3.0 |
| | 2.0 | 10 | 4.2 |
| HA-PEG-TA | 0.5 | 62 | 8.9 |
| | 1.0 | 36 | 10.5 |
| | 2.0 | 15 | 12.5 |
| CMC-PEG-TA | 0.5 | 145 | 5.1 |
| | 1.0 | 71 | 5.9 |
| | 2.0 | 42 | 6.2 |
| ALG-PEG-TA | 0.5 | 81 | 2.7 |
| | 1.0 | 39 | 3.1 |
| | 2.0 | 18 | 7.3 |

TABLE 8

| | Amounts of iron-containing polymer particles (g) 369 ug of HRP/g of bead | Hydrogel formation time (sec) | Hydrogel mechanical strength (KPa) |
|---|---|---|---|
| Tet-TA | 0.2 | 52 | 10.2 |
| | 0.4 | 21 | 11.9 |
| | 0.8 | 10 | 13.2 |
| GHPA | 0.2 | 26 | 5.3 |
| | 0.4 | 11 | 9.2 |
| | 0.8 | <5 | 13.4 |
| CHPA | 0.2 | 62 | 1.3 |
| | 0.4 | 42 | 3.1 |
| | 0.8 | 20 | 5.7 |
| GPEG-TA | 0.2 | 39 | 8.1 |
| | 0.4 | 17 | 10.1 |
| | 0.8 | 6 | 11.9 |
| CPTA | 0.2 | 34 | 2.0 |
| | 0.4 | 17 | 3.3 |
| | 0.8 | <5 | 5.1 |
| HA-PEG-TA | 0.2 | 39 | 10.1 |
| | 0.4 | 16 | 11.4 |
| | 0.8 | 6 | 13.8 |
| CMC-PEG-TA | 0.2 | 83 | 6.2 |
| | 0.4 | 44 | 7.5 |
| | 0.8 | 24 | 8.0 |
| ALG-PEG-TA | 0.2 | 52 | 3.7 |
| | 0.4 | 22 | 5.1 |
| | 0.8 | 12 | 8.3 |

<Experimental Example 2> Cytotoxicity Test

For the cytotoxicity evaluation, the Tet-TA polymer of Example 5-1 was used to prepare a hydrogel according to the method of Example 6. Then, a fibroblast was cultured inside the formed hydrogel, so as to evaluate the cytotoxicity. The concentration of the cells used herein was $1 \times 10^5$ cells/well, and the cultured cells were dyed using the live/dead analysis kit, and observed with a fluorescent microscope.

Figure 14:
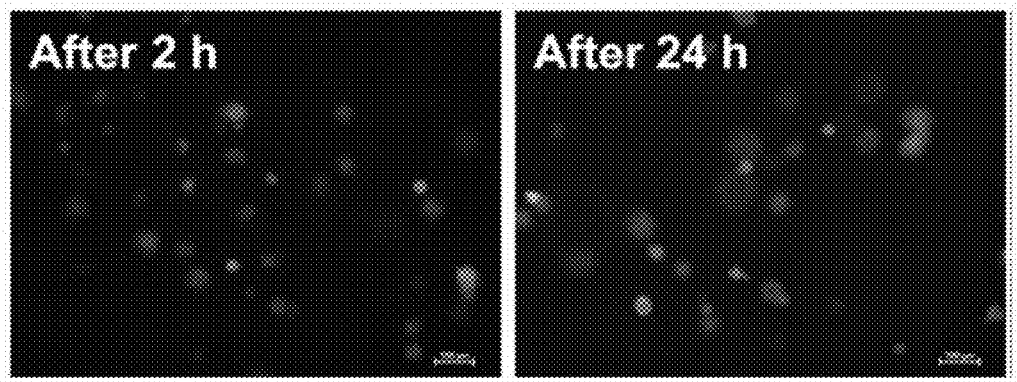
FIG. 14 is a diagram showing results of cytotoxicity test on a hydrogel according to an exemplary embodiment.

The observation results are shown in FIG. 14. Referring to FIG. 14, excellent cell adhesion and cell proliferation were confirmed, referring that the formed hydrogel herein had excellent cell suitability.

<Experimental Example 3> Review on Releasing Power of Physiologically Active Substances The in situ-forming hydrogel prepared according to the enzyme immobilization method was used to perform evaluation of release behavior of growth factors. To carry out the experiment, the Tet-TA polymer of Example 5-1 was used to prepare a hydrogel according to the method of Example 6. Here, the concentration of the introduced growth factor (bFGF) was 300 ng/mL, and the evaluation was carried out for 1 week.

Figure 15:
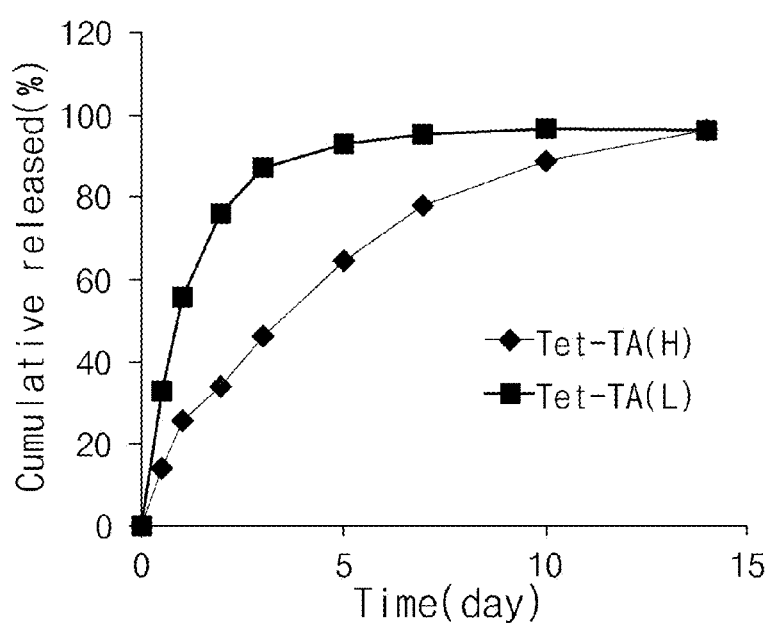
FIG. 15 is a diagram showing results of reviewing releasing power of hydrogel growth factors according to an exemplary embodiment.

Accordingly, as shown in FIG. 15, it was confirmed that the growth factor was released in a sustained manner in the in situ-forming hydrolysis prepared according to the enzyme immobilization method. In addition, since the hardening strength of the hydrogel can be adjusted by adjusting the concentration of hydrogen peroxide or the polymer, the release behavior of the drug can be slowed down due to higher mechanical strength in accordance with increased hardening strength (H). Alternatively, the release behavior of the drug can accelerated due to lower mechanical strength in accordance with decreased hardening strength (L). That is, the control in the release speed of the drug was achieved.

As a result, it was confirmed that the in situ-forming hydrolysis prepared according to the enzyme immobilization method can be used as a carrier for a physiologically active substance, e.g., a growth factor, in an efficient manner.

<Experimental Example 4> Review on Tissue Adhesion Strength

The adhesive strength of the hydrogel was comparatively compared using the universal testing machine (UTM). Here, fibrin glue, which is currently the most widely used, was used as a control group of the experiment. The results are shown in FIG. 16.

Figure 16:
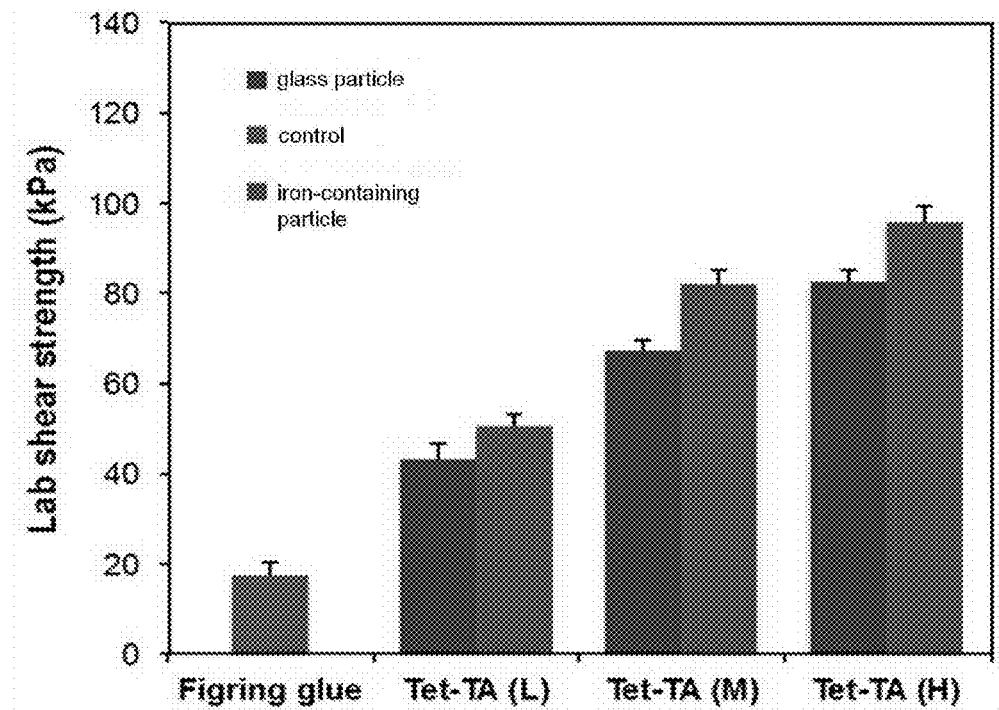
FIG. 16 is a diagram showing results of testing tissue adhesion strength of a hydrogel according to an exemplary embodiment.

Referring to FIG. 16, the Tet-TA (10 wt %) hydrogel prepared according to the immobilization method showed the adhesion strength in a range from about 45 KPa to about 83 KPa, the adhesion strength being 3 to 6 times greater as much as the adhesion strength of the control group (fibrin glue). In addition, the adhesion strength of the hydrogel using the iron-containing particle was greater than that of the hydrogel using the glass particle by about 52 KPa to about 95 KPa. In the case of the hydrogel using the microparticle, the amount of hydrogen peroxide (L: 0.016 wt %, M: 0.063 wt %, H: 0.25 wt %) was adjusted to confirm the capability of adjusting the tissue adhesion strength.

<Experimental Example 5> Review on Reusability 2,2'-azobis-(3-ethylbenzothiazoline-6-sulfonic acid (ABTS) reagent, which can confirm capability to produce radicals and to capability to induce oxidation reaction, was used to confirm reusability of the immobilized HRP according to the number of gel-forming injection. A hydrogel was prepared by using the Tet-TA polymer of Example 5-1 according to the method of Example 6, and after the gel formation, the microparticle placed in the inner space of the syringe was sufficiently washed with PBS, to proceed the experiment that determines the reusability of the immobilized enzyme.

Figure 17:
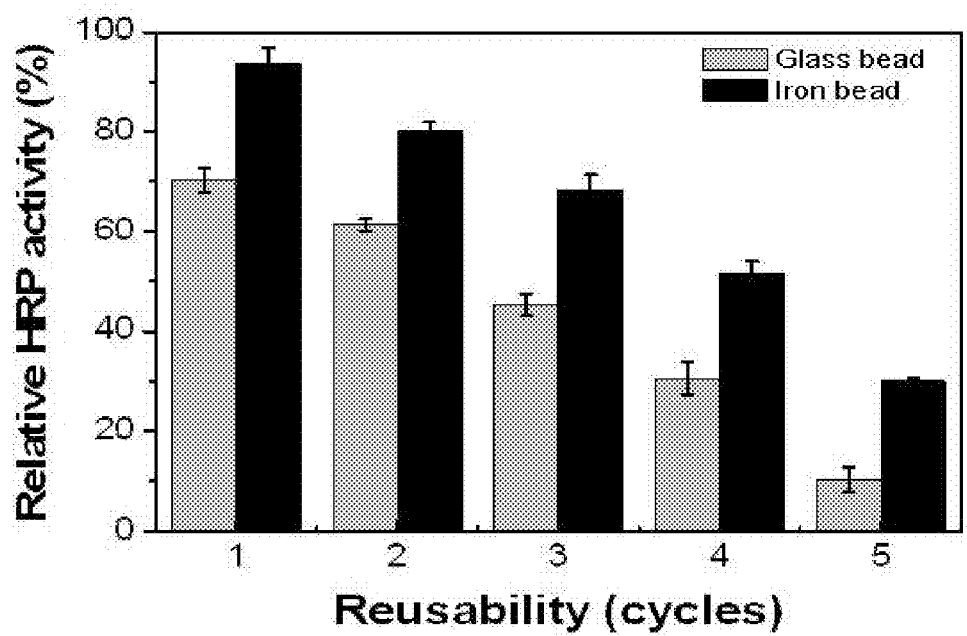
FIG. 17 is a graph showing results of testing reusability of microparticles in formation of a hydrogel according to an exemplary embodiment.

Accordingly, as shown in FIG. 17, it was confirmed that the HRP immobilized on the particle showed its activity of about 40% to about 60% according to the types of the microparticles, even if the number of times to re-use of the immobilized enzyme increased. In this regard, it was confirmed that the immobilized enzyme can be continuously used in the form of an injectable gel-forming agent using the various types of the microparticles according to exemplary embodiments of the inventive concept.

While the inventive concept has been particularly shown and described with reference to exemplary embodiments thereof, it will be understood that various changes in form and details may be made therein without departing from the spirit and scope of the following claims.

INDUSTRIAL APPLICABILITY

The in suit-forming hydrogel can be used as an injectable hydrogel system in a living body. The injectable hydrogel system can form a hydrogel in the body including a desired tissue, organ, or body cavity, so as to fill a defect site or depression in the body. In addition, through a simple mixing of many therapeutic drugs, the injectable hydrogel system can be used as a carrier for delivering a physiologically active or a drug, such as a peptide, a protein, and DNA, and in transporting nutrients to cells and products.

The invention claimed is:

1. A method of preparing a hydrogel, the method comprising:
    stirring together a glycidyl methacrylate (GMA) monomer, a methyl methacrylate (MMA) monomer, an ethyleneglycol dimethacrylate (EGDMA) cross-linking agent, and an iron containing compound to make a copolymer with the iron containing compound;
    immobilizing an enzyme onto the copolymer containing iron to prepare an enzyme-immobilized support;
    cross-linking a polymer in the presence of hydrogen peroxide and in the presence of the enzyme-immobilized support to form the hydrogel, wherein the polymer comprises a phenol or aniline functional group at a side chain; and
    separating the hydrogel away from the enzyme-immobilized support.

2. The method of claim 1, wherein the enzyme is one or two selected from the group consisting of horseradish peroxidase, glutathione peroxidase, haloperoxidase, myeloperoxidase, catalase, hemoprotein, peroxiredoxin, animal heme-dependent peroxidases, thyroid peroxidase, vanadium bromoperoxidase, lactoperoxidase, tyrosinase, and catechol oxidase.

3. The method of claim 1, wherein the enzyme-immobilized support is in the form of a microparticle, a porous sponge, or a porous sheet.

4. The method of claim 1, wherein the enzyme comprises horseradish peroxidase.

5. The method of claim 1, wherein the polymer also comprises a spacer selected from the group consisting of polyethylene glycol (PEG), polyethylene oxide (PEO), polyethylene amine (PEI), polyvinyl alcohol (PVA), and polyacrylic acid (PAA).

6. The method of claim 1, wherein the polymer is selected from the group consisting of a four arm polypropylene oxide-polyethylene oxide polymer-tyramine (Tet-TA) polymer, a gelatin-hydroxyphenylacetate (GHPA) polymer, a chitosan-hydroxyphenylacetic acid (CHPA) polymer, a gelatin-poly(ethylene glycol)-tryamine (GPEG-TA) polymer, a chitosan-poly(ethylene glycol)-tyramine (CPTA) polymer, a hyaluronic acid-poly(ethylene glycol)-tyramine (HA-PEG-TA) polymer, a carboxymethyl cellulose-poly(ethylene glycol)-tyramine (CMC-PEG-TA) polymer, and an alginate-polyethylene glycol)-tyramine (ALG-PEG-TA) polymer.

7. The method of claim 1, wherein cross-linking is achieved by introducing the polymer with the hydrogen peroxide into a chamber containing the enzyme-immobilized support.

8. The method of claim 1, wherein cross-linking is achieved by introducing the enzyme-immobilized support into a chamber containing the polymer with the hydrogen peroxide.

9. The method of claim 1, wherein separating the hydrogel away from the enzyme-immobilized support is achieved by extruding the hydrogel through a filter which restricts the enzyme-immobilized support from extruding through the filter.

10. A method of preparing a hydrogel, the method comprising:
modifying a support with a catechol derivative, wherein the catechol derivative is selected from the group consisting of 3,4-dihydroxy hydrocinnamic acid, dopamine, chloroacetylcatechol, aminomethylcatechol, deoxyepinephrine, dihydroxybenzohydrazine, caffeic acid phenethylester, and hirsutenone;
binding an enzyme onto a functional group of the catechol derivative, after modifying the support, to prepare an enzyme-immobilized support;
cross-linking a polymer to form the hydrogel in the presence of hydrogen peroxide and in the presence of the enzyme-immobilized support, wherein the polymer comprises a phenol or aniline functional group side chain; and
separating the cross-linked polymer away from the enzyme-immobilized support by extruding the cross-linked polymer through a filter to obtain the hydrogel in which the filter restricts the enzyme-immobilized support from extruding through the filter.

11. The method of claim 10, wherein the polymer is selected from the group consisting of a four arm polypropylene oxide-polyethylene oxide polymer-tyramine (Tet-TA) polymer, a gelatin-hydroxyphenylacetate (GHPA) polymer, a chitosan-hydroxyphenylacetic acid (CHPA) polymer, a gelatin-poly(ethylene glycol)-tryamine (GPEG-TA) polymer, a chitosan-poly(ethylene glycol)-tyramine (CPTA) polymer, a hyaluronic acid-poly(ethylene glycol)-tyramine (HA-PEG-TA) polymer, a carboxymethyl cellulose-poly (ethylene glycol)-tyramine (CMC-PEG-TA) polymer, and an alginate-polyethylene glycol)-tyramine (ALG-PEG-TA) polymer.

12. The method of claim 10, wherein the enzyme is at least one selected from the group consisting of horseradish peroxidase, glutathione peroxidase, haloperoxidase, myeloperoxidase, catalase, hemoprotein, peroxiredoxin, animal heme-dependent peroxidases, thyroid peroxidase, vanadium bromoperoxidase, lactoperoxidase, tyrosinase, and catechol oxidase.

13. The method of claim 10, wherein the enzyme comprises horseradish peroxidase.

14. The method of claim 10, wherein the support is in the form of a microparticle, a porous sponge, or a porous sheet.

15. The method of claim 10, wherein the support in the form of the microparticle is non-porous or porous and is selected from a glass particle, a metal particle, a polymer particle, or a mixed particle thereof.

16. The method of claim 10, wherein the functional group of the catechol derivative is selected from the group consisting of a carboxyl group, an amine group, a hydroxyl group, an aldehyde group, an epoxy group, a thiol group, a maleimide group, a carbonate ester group, a cyano group, an acrylic group, an acetylene group, and a diazolyl group.

17. A method of preparing a hydrogel, the method comprising:
modifying a support with a silane derivative, wherein the silane derivative is selected from the group consisting of 3-aminopropyl triethoxysilane, trimethoxy (7-octane-1-yl) silane, vinyltrimethoxysilane, 3-trimethoxysilyl-1-propanethiol, 3-aminopropyl trimethoxysilane, aminoethyl trimethoxysilyl propylamine, triethoxyvinylsilane, isocyanatopropyl triethoxysilane, cyanoethyl triethoxysilane, mercaptopropyl triethoxysilane, and triethoxysylylpropyl diethanolamine;
binding an enzyme onto a functional group of the silane derivative, after modifying the support, to prepare an enzyme-immobilized support;
cross-linking a polymer, to form the hydrogel, in the presence of hydrogen peroxide and in the presence of the enzyme-immobilized support, wherein the polymer comprises a phenol or aniline side chain functional group; and
separating the cross-linked polymer away from the enzyme-immobilized support by extruding the cross-linked polymer through the filter to obtain the hydrogel in which the filter restricts the enzyme-immobilized support from extruding through the filter.

18. The method of claim 17, wherein the polymer is selected from the group consisting of a four arm polypropylene oxide-polyethylene oxide polymer-tyramine (Tet-TA) polymer, a gelatin-hydroxyphenylacetate (GHPA) polymer, a chitosan-hydroxyphenylacetic acid (CHPA) polymer, a gelatin-poly(ethylene glycol)-tryamine (GPEG-TA) polymer, a chitosan-poly(ethylene glycol)-tyramine (CPTA) polymer, a hyaluronic acid-poly(ethylene glycol)-tyramine (HA-PEG-TA) polymer, a carboxymethyl cellulose-poly (ethylene glycol)-tyramine (CMC-PEG-TA) polymer, and an alginate-polyethylene glycol)-tyramine (ALG-PEG-TA) polymer.

19. The method of claim 17, wherein the enzyme is at least one selected from the group consisting of horseradish peroxidase, glutathione peroxidase, haloperoxidase, myeloperoxidase, catalase, hemoprotein, peroxiredoxin, animal heme-dependent peroxidases, thyroid peroxidase, vanadium bromoperoxidase, lactoperoxidase, tyrosinase, and catechol oxidase.

20. The method of claim 17, wherein the support in the form of the microparticle is non-porous or porous glass particle.

* * * * *